United States Patent [19]

Spietschka et al.

[11] Patent Number: 4,599,408
[45] Date of Patent: Jul. 8, 1986

[54] PERYLENE-3,4,9,10-TETRACARBOXYLIC ACID MONOANHYDRIDE MONOIMIDES

[75] Inventors: Ernst Spietschka, Idstein; Helmut Tröster, Königstein, both of Fed. Rep. of Germany

[73] Assignee: Hoechst Aktiengesellschaft, Frankfurt, Fed. Rep. of Germany

[21] Appl. No.: 599,202

[22] Filed: Apr. 11, 1984

Related U.S. Application Data

[63] Continuation of Ser. No. 261,454, May 7, 1981, abandoned.

[30] Foreign Application Priority Data

May 5, 1980 [DE] Fed. Rep. of Germany ....... 3017185

[51] Int. Cl.[4] .......................... C07D 491/06
[52] U.S. Cl. .......................... 544/125; 546/37
[58] Field of Search .......................... 546/37; 544/125

[56] References Cited

U.S. PATENT DOCUMENTS 4,250,079 2/1981 Babler .......................... 260/42.21

FOREIGN PATENT DOCUMENTS 411217 of 0000 Fed. Rep. of Germany ........ 546/37

OTHER PUBLICATIONS

Nagao et al., Chem. Abstracts (I), vol. 91(4), Abst. No. 22404r Jul. 23, 1979.
Nagao et al., Chem. Abstracts (II) vol. 91(5), Abst. No. 38468a Jul. 30, 1979.
Nagao et al., Chem. Abstracts (III), vol. 76(11), Abst. No. 59297z, Mar. 13, 1972.
Nagao et al., Chem. Abstracts (IV), vol. 75, (23), Abst. No. 140,549j, Dec. 6, 1971.
Chemistry Letters, No. 2 (1979), pp. 151-154.

*Primary Examiner*—Alan L. Rotman
*Attorney, Agent, or Firm*—Curtis, Morris & Safford

[57] ABSTRACT

Compounds of the formula

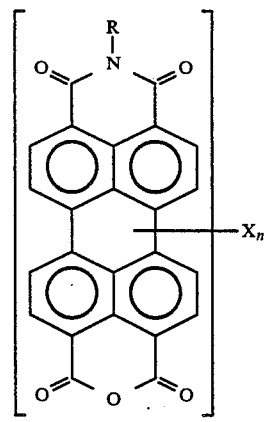

in which R denotes hydrogen, hydroxyl, amino or optionally substituted alkyl, X denotes chlorine or bromine and n is a number from zero to 4, are obtained from the corresponding mono-alkali metal salts of perylene-3,4,9,10-tetracarboxylic acid monoanhydrides by reaction with compounds of the formula $R-NH_2$, in which R has the above meaning, at 0°-130° C. The compounds are colorants or starting materials for colorants.

4 Claims, No Drawings

PERYLENE-3,4,9,10-TETRACARBOXYLIC ACID MONOANHYDRIDE MONOIMIDES

This application is a continuation of application Ser. No. 261,454, abandoned, filed May 7, 1981.

The invention relates to perylene-3,4,9,10-tetracarboxylic acid monoanhydride monoimides of the formula 1

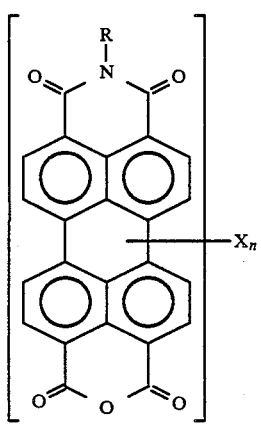

in which R denotes hydrogen, hydroxy, amino, cycloalkyl with 4 to 8 C atoms or alkyl which has 1 to 8 C atoms, unsubstituted or substituted by cycloalkyl with 4 to 8 C atoms, phenyl, or phenyl substituted by halogen, lower alkyl, lower alkoxy or lower alkoxycarbonyl, or R is alkyl of 1 to 8 C atoms, substituted by cyano, hydroxy, carbamoyl, acyl, lower dialkylamino, morpholyl, piperidyl or alkoxy which has 1 to 8 C atoms, unsubstituted or substituted by hydroxy, lower alkoxy, lower hydroxyalkyl, cyano, cycloalkyl with 4 to 8 C atoms or phenyl, X denotes chlorine or bromine and n denotes a number from 0 to 4, and in which R does not denote the group

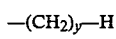

in which y is a number from 0 to 4, if n is zero.

Those compounds in which n denotes 0 are particularly preferred.

The invention also relates to a process for the preparation of perylene-3,4,9,10-tetracarboxylic acid monoanhydride monoimides of the formula 1, in which R represents hydrogen, amino, hydroxy, or an optionally substituted alkyl group, X denotes chlorine or bromine and n denotes a number from 0 to 4.

The preparation of perylene-3,4,9,10-tetracarboxylic acid monoanhydride monoimide by partial saponification of the corresponding diimide with sulfuric acid is known (German Patent Specification 411,217). However, the process gives a yield of only 55% (Nagao et al., Kogyo Kagaku Zasshi 1971, 74 (12), pages 2,500 to 2,502).

The reaction of perylene-3,4,9,10-tetracarboxylic acid dianhydride with alkylamines, which leads to the diimides via the monoimides, is investigated in Nippon Kagaku Kaishi, 1979 (4), pages 528-34. The monoimides intermediate formed are determined in the reaction mixture by spectrophotometry, maximum yields of 62-84% being given (paragraphs 2.3 and 2.4, page 529, and Table 3, page 530). The yields actually achieved for the monoimides isolated from the reaction mixture were, however, only 24-46% (paragraph 2.2 and Table 1, page 529). Besides the unsatisfactory yields, this procedure has the disadvantage that it requires continuous analytical examination of the course of the reaction.

It has now been found that perylene-3,4,9,10-tetracarboxylic acid monoanhydride monoimides of the formula 1 can be obtained by a process which comprises reacting mono-alkali metal salts of perylene-3,4,9,10-tetracarboxylic acid monoanhydrides, of the formula 2

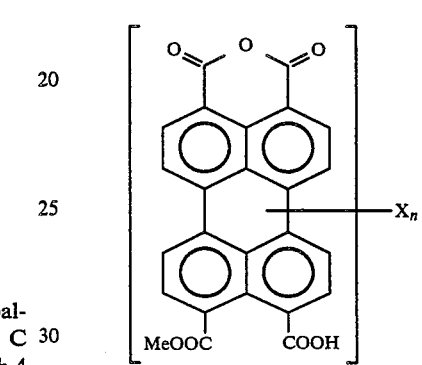

in which Me represents a sodium or potassium atom and X and n have the abovementioned meaning, with compounds of the formula 3

$$R-NH_2 \qquad (3)$$

wherein R denotes hydrogen, amino, hydroxy or an optionally substituted alkyl group, at 0°–130° C., preferably at 0°–95° C.

The new process gives the corresponding perylene-3,4,9,10-tetracarboxylic acid monoanhydride monoimides in high, in some cases almost quantitative, yields in a simple manner, without special monitoring of the course of the reaction being necessary.

Preferred embodiments of the invention are described in more detail below:

The starting compounds of the formula 2 can be prepared by the process described in U.S. patent application Ser. No. 239,909, filed Mar. 3, 1981. In this process, three equivalents of acid, such as hydrochloric acid, sulfuric acid, nitric acid or phosphoric acid, are added to an aqueous solution or suspension of a tetra-alkali metal salt or tetraammonium salt of the corresponding perylene-3,4,9,10-tetracarboxylic acid at about 20°–100° C., preferably 70°–95° C. If an ammonium salt is employed, at least one equivalent of sodium or potassium ions must be present. Intermediate isolation of these compounds is not necessary. It is thus possible for them to be reacted with the compounds of the formula 3 in the form in which they are obtained in the reaction mixture during synthesis.

Particularly preferred starting substances of the formula 2 are those in which n denotes 0 and Me denotes potassium.

More specifically, the starting materials of the formula 2 are prepared by reacting salts of perylene-3,4,9,10-tetracarboxylic acid of the formula 4

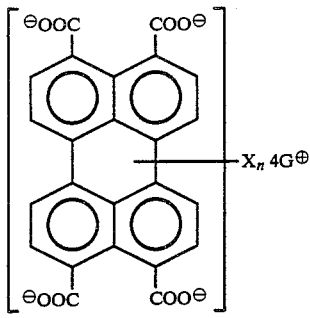

wherein
G+ is a cation and
X and n are defined as for formula 1 or preferably represent a tetraalkali metal or tetraammonium salt, in aqueous solution or suspension, if necessary in the presence of at least one molar equivalent of Me+, at a temperature of from 20° to 100° C., preferably 70° to 95° C., with three molar equivalents of an acid.

This process is suitably performed in the following manner: The perylenetetracarboxylic acid or its anhydride is converted in water into the tetracarboxylate in usual manner at elevated temperature by adding the required quantity of a base. This reaction gives a suspension or solution, depending on the dilution degree. If the base used for the conversion into the tetracarboxylate is an amine, there has to be added at least the cation equivalent thereof, which is necessary for the monoalkali metal salt formation, in the form of a hydroxide or of a corresponding salt.

Excess base, if any, is neutralized with an acid, whereupon there are added 3 equivalents of acid per mol of perylenetetracarboxylic acid at 20° to 100° C., preferably at 70° to 95° C. When the acid addition is performed without heat supply, the reaction mixture is suitably heated thereafter to effect the conversion into the monoanhydride. Alternatively, the reaction product may be isolated without previous heating. During drying, it is converted into the monoanhydride.

The addition rate of acid is suitably adjusted such that the pH does not drop below 3, in order to reach a high purity of the product, the pH being preferably adjusted to a range of from 4 to 7.

The acid demand is given by the end point of the protonization, which is characterized by the fact that the pH jumps to 3.5–6.5.

The precipitated difficulty soluble monoalkali metal salt of perylene-3,4,9,10-tetracarboxylic acid monoanhydride may be isolated in usual manner by filtration.

Alternatively, it may be further reacted without intermediate isolation.

Suitable bases for dissolving the perylene-3,4,9,10-tetracarboxylic acid are in particular the hydroxides and carbonates of sodium and potassium. Suitable amines are secondary and tertiary amines that are sufficiently basic for a conversion of perylenetetracarboxylic acid into its tetraammonium salt. Examples of amines are dimethyl amine, dibutyl amine, trimethyl amine, triethyl amine, diethanol amine or triethanol amine.

Suitable alkali metal ion donors are the hydroxides, chlorides, sulfates, nitrates or carbonates of sodium, in particular of potassium.

Suitable acids are strong mineral acids such as hydrochloric, sulfuric, nitric and phosphoric acid. Alternatively, there may be used acid salts such as sodium- or potassium hydrogen sulfate as well as organic acids such as acetic acid, propionic acid, trichloroacetic acid or toluenesulfonic acid.

The following examples illustrate the preparation of the starting materials of the formula 2. Percentages are by weight unless otherwise stated.

EXAMPLE 1

19.6 g of perylene-3,4,9,10-tetracarboxylic acid dianhydride and 8.3 g of 100% sodium hydroxide are dissolved in 2,500 ml of water at 80° C., whereupon the pH of the resultant solution is adjusted to 4.5 by adding dropwise 61 g of 10% hydrochloric acid at this temperature over a period of about 2 hours (single-cell-pH-meter). The suspension obtained is stirred for 2 hours at 80° C., during which period its pH rises only slightly to about 5.0. The reaction product is suction-filtered at 20°–25° C., washed chloride-free with water and dried.

Yield: 21.3 g.

Analysis: calc. Na: 5.3%; found Na: 3.5% ≙ 65.7% of the theory.

EXAMPLE 2

196 g of perylene-3,4,9,10-tetracarboxylic acid dianhydride are dissolved in 2,240 g of a 5% potassium hydroxide solution at 90° C. The resulting solution has a pH of about 10.5 (single-cell-pH-meter).

1,432 g of a 10% phosphoric acid are added dropwise over a period of 2–3 hours at 90° C., whereupon the pH has dropped to 5.0. The suspension is stirred for 1 hour at the same temperature, during which operation the pH remains practically unchanged. The precipitated bordeaux-colored potassium salt is suction-filtered at 20°–25° C., washed phosphate-free with water and dried at 110° C.

Yield: 220 g.

| Analysis: | | | |
|---|---|---|---|
| calc. C: 64.3% | | found C: 63.7% | |
| H: 2.0% | | H: 2.0% | |
| K: 8.7% | | K: 8.6% | |

The same good results are obtained when using instead of the 10% phosphoric acid the equivalent quantity (168 g) of a 85% phosphoric acid.

EXAMPLE 3

A mixture of 196 g of perylene-3,4,9,10-tetracarboxylic acid dianhydride, 2,000 ml of water and 132.9 g of 85% potassium hydroxide is heated to 90° C., during which operation the pH is 10–11. Thereafter the pH is adjusted to a practically constant value of 4.5–5.0 by adding dropwise 180 g of 31% hydrochloric acid at 90° C. over a period of about 2 hours. The suspension obtained is stirred for 1 hour and the precipitated potassium salt is suction-filtered while still hot and subsequently washed with hot water until free from chloride ions. Drying gives 219 g of a dark-red product, which is identical with the reaction product of Example 2.

EXAMPLE 4

19.6 g of perylene-3,4,9,10-tetracarboxylic acid dianhydride are added to a solution of 27.8 g of triethylamine in 500 ml of water and dissolved therein by heating to 80° C. 3.8 g of potassium chloride are added to the clear solution and subsequently there are added dropwise, at 80° C. over a period of 2–3 hours, 185 ml of 1N-hydrochloric acid, a practically constant pH of 4–5 is established during this operation. A spot test using filter paper reveals a practically colorless solution. The product is stirred for about 2 hours at 80° C. and thereafter the precipitated dark-red microcrystalline potassium salt is isolated in usual manner.

Yield: 21.9 g.
Analysis: K: 7.6% ≙ 87.3% of the theory.

EXAMPLE 5

19.6 g of perylene-3,4,9,10-tetracarboxylic acid dianhydride are suspended in 2,500 ml of water and subsequently dissolved therein by adding 8.0 g of sodium hydroxide at 80° C. After addition of 3.8 g of potassium chloride the pH is adjusted to 7.5 with 1N-hydrochloric acid and subsequently to a practically constant value of 4.5 by adding dropwise, over a period of about 2 hours, at 80° C., 150 ml of 1N-hydrochloric acid. After a stirring time of one hour the reaction product precipitated in the form of bordeaux-colored needles is isolated.

Yield: 21.5 g.
Analysis: K: 6.7%; Na 0.55% ≙ 87.3% of the theory (calculated on monoalkali metal salt).

EXAMPLE 6

38.6 g of 50% acetic acid are slowly added dropwise to 550 g of an aqueous solution containing 0.1 mol of the tetrapotassium salt of perylene-3,4,9,10-tetracarboxylic acid, at 90° C., until a practically constant pH of 6.2 is obtained. After a 1.5 hour's stirring time at 90° C. the product is suction-filtered in hot state and washed with hot water, which gives 43.8 g of monopotassium salt. The product corresponds to that obtained in Example 2.

EXAMPLE 2

547.5 g of 10% hydrochloric acid are obtained dropwise, at 20°–25° C., over a period of 30 minutes, to 2,600 ml of an aqueous solution containing 0.5 mol of the tetrapotassium salt of perylenetetracarboxylic acid. The batch is heated to 90° C. and maintained at this temperature for 30 minutes. The resulting reaction product corresponds to that obtained in Example 2.

Yield: 218 g.

EXAMPLE 8

109 g of 10% hydrochloric acid are added dropwise, at 20°–25° C., within about 3 hours, to 606.3 g of a 0.1 molar solution of the tetrapotassium salt of perylenetetracarboxylic acid. The pH of the solution is 6–7. Subsequently the pH is adjusted to 5.0–5.5 by adding 1 g of 10% hydrochloric acid. After some hours the reaction product is isolated in usual manner and dried.

Yield: 42.5 g.
Analysis: K: 7.8% ≙ 89.6% of the theory.

EXAMPLE 9

23.6 g of bromoperylenetetracarboxylic acid dianhydride (bromine content 14.4% ≙ 0.82 Br atoms) are dissolved in 500 ml of water by adding 13.2 g of 88% potassium hydroxide at 80° C. The pH is subsequently adjusted to 4–5 by adding dropwise 56 g of 10% hydrochloric acid at 80° C. The potassium salt obtained is isolated after 1 hour.

Yield: 25.7 g.
Analysis: K: 6.6%; Br: 12.8%.

The bromoperylenetetracarboxylic acid dianhydride was prepared according to Example 1 of German Offenlegungsschrift 2,519,790 using, however, instead of chlorine, the equivalent quantity of bromine.

EXAMPLE 10

26.5 g of tetrachloroperylenetetracarboxylic acid dianhydride (chlorine content 27.2%), prepared according to Example 3 of German Offenlegungsschrift 2,519,790, are dissolved at 80° C. in 500 ml water and 13.2 g of 85% potassium hydroxide. The pH is subsequently adjusted to 3–4 by adding dropwise 57 g of 10% hydrochloric acid, at the above temperature and the precipitated reaction product is isolated from the hot solution after stirring for 1 hour. 25.7 g of the corresponding monoanhydride monopotassium salt are obtained.

Analysis: Cl: 24.5%. K: 6.3%.

Examples of starting substances of the formula 3 are ammonia, hydrazine, hydroxylamine, methyl-, ethyl-, propyl-, butyl- and octyl-amie, benzylamine, ethanol-, isopropanol- and hydroxypropyl-amine, methoxypropyl-, butoxypropyl-, butoxyethoxypropyl-, octyloxypropyl-, 2-ethylhexyloxypropyl- and 3-morpholinopropyl-amine, cyclohexylamine, 2-cyanoethylamine, 2-chloro- or -bromoethylamine, carbamoylethylamine and cyclohexyloxypropyl and benzyloxypropyl-amine.

At least 2 moles, preferably 3 moles or even a larger excess, of the compound 3 are employed per mole of starting substance of the formula 2. The condensation is carried out in water at temperatures from 0° to 130° C., preferably at 0°–95° C. It is expedient to follow a procedure which comprises introducing the mono-alkali metal salt of the monoanhydride into an amine/water mixture, or adding the amine of the formula 3 to an aqueous suspension of the mono-alkali metal salt of the monoanhydride.

The reactants can be combined at 0°–95° C. It is expedient to prepare the reaction mixture at lower temperatures of about 0°–30° C. and then to bring the condensation reaction to completion at higher temperatures of about 70°–95° C. The reaction to give the monoimide has in general ended after 1–2 hours at 90°–95° C.

The reaction product is then obtained from the reaction mixture by acidification, for example with mineral acids, preferably at the higher temperature of about 70°–95° C. It is isolated in the customary manner, for example by filtration. If necesary, the product can also be freed from small amounts of diimide which have also been formed and from perylenetetracarboxylic acid dianhydride, for example in accordance with the statements made in Nippon Kagaku Kaishi loc. cit. paragraph 2.2, page 529, by a procedure in which the alkali-insoluble diimide is removed by alkaline clarifying filtration and the perylenetetracarboxylic acid dianhydride is separated off, via its readily soluble tetrapotassium salt, from the dipotassium salt of the end product, which is frequently sparingly soluble.

Most of the process products obtained are new. They are valuable starting materials for the preparation of colorants. However, they can also themselves be used as colorants, if necessary after appropriate conditioning.

In the following examples, the percentage data relate to the weight, unless indicated otherwise.

EXAMPLE 11

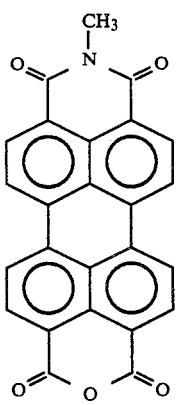

10.3 g of methylamine solution (45.4% strength) are poured into a suspension of 22.4 g of the monopotassium salt of perylene-3,4,9,10-tetracarboxylic acid monoanhydride in 250 ml of water at 0°–5° C., and the mixture is stirred at 0°–5° C. for 12 hours. 27.0 g of 50% strength potassium hydroxide solution are then added, and the temperature of the mixture is kept at 90° C. for 1 hour. The reaction product is filtered off at 20°–25° C. and, in order to remove traces of the tetra-potassium salt of the perylenetetracarboxylic acid, is washed with 5% strength potassium hydroxide solution until the filtrate runnings are colorless. The residue on the filter is dissolved in 300 ml of water at 90°–95° C., and traces of the perylenetetracarboxylic acid diimide are filtered off hot. Perylene-3,4,9,10-tetracarboxylic acid monoanhydride monomethylimide is precipitated from the filtrate by acidification with concentrated hydrochloric acid, filtered off, washed until free from chloride and dried.

Yield: 19.4 g (95.8% of theory)

| Analysis: | | | | |
|---|---|---|---|---|
| calculated: | C | 74.1% | found: | C 73.7% |
| | H | 2.7% | | H 2.8% |
| | N | 3.5% | | N 3.5% |

EXAMPLE 12

124 g of methylamine (45.4% strength) are added at 20°–25° C. to a suspension of the mono-potassium salt of perylenetetracarboxylic acid monoanhydride, which has been obtained from 196 g of perylenetetracarboxylic acid dianhydride (without intermediate isolation of the mono-potassium salt) according to Example 3. The mixture is then warmed to 90°–95° C. After 1 hour, 160 g of 50% strength potassium hydroxide solution are allowed to run in and the mixture is subsequently stirred for a further hour at the same temperature.

The red di-potassium salt, which has crystallized out, of the monomethylimide is filtered off at room temperature, washed with an aqueous solution of 3% of potassium chloride and 1% of potassium hydroxide until the filtrate runnings are colorless, and worked up as indicated in Example 18 to give an identical end product.

Yield: 191.7 g (94.7% of theory, relative to the perylenetetracarboxylic acid dianhydride)

EXAMPLE 13

If the procedure followed is as indicated in Example 18, but the mono-sodium salt (Na content of 3.5% = 65.8% of mono-sodium salt) is used instead of the mono-potassium salt, 13.0 (64.2%) of an identical end product are obtained.

EXAMPLE 14

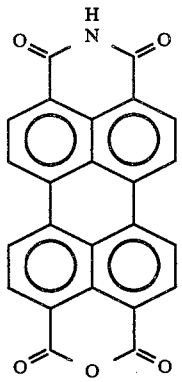

22.4 g of the mono-potassium salt of perylenetetracarboxylic acid monoanhydride are introduced into 280 g of aqueous 3% strength ammonia solution at 0°–5° C., and the mixture is subsequently stirred for 4 hours, without further cooling. The mixture is then warmed to 90°–95° C. and stirred at this temperature for 2 hours. After the addition of a solution of 15 g of potassium carbonate (anhydrous) in 50 ml of water, the mixture is stirred for a further hour at 90° C. The product is filtered off at 20°–25° C. and, in order to remove a small amount of the tetra-potassium salt of the perylenetetracarboxylic acid, is washed with 2% strength potassium carbonate solution until the filtrate runnings are colorless.

The residue is dissolved in 1,300 g of 3.5% strength potassium hydroxide solution at 95° C., and a trace of perylenetetracarboxylic acid diimide is separated off by filtration. The reaction product is precipitated from the hot filtrate with hydrochloric acid (31% strength) and isolated in the customary manner. 17.9 g (91.6%) of perylenetetracarboxylic acid monoanhydride monoimide are obtained.

Analysis: calculated: N 3.5% found: N 3.5%

EXAMPLE 15

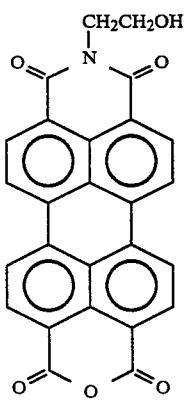

22.4 g of the mono-potassium salt of perylenetetracarboxylic acid monoanhydride are introduced into an aqueous solution of 13.5 g of ethanolamine in 250 ml of water, and the mixture is stirred at 20°-30° C. for 2 hours and at 90°-95° C. for 2 hours. The dark red solution is then clarified hot and the reaction product is precipitated by acidification and isolated in a known manner. To remove a small amount of perylenetetracarboxylic acid, the product is warmed to 90° C. in 200 ml of 5% strength potassium hydroxide solution and the di-potassium salt is salted out by adding 20 g of potassium chloride. The product, which is filtered off at room temperature, is washed with an aqueous solution of 3% of potassium chloride and 1% of potassium hydroxide, the residue is dissolved in 500 ml of water and the product is precipitated under acid conditions and isolated, in the customary manner.

Yield: 20.0 g (91.9%)

| Analysis: | | | | | |
|---|---|---|---|---|---|
| calculated: | C | 71.7% | found: | C | 71.0% |
| | H | 3.0% | | H | 3.0% |
| | N | 3.2% | | N | 3.2% |

EXAMPLE 6

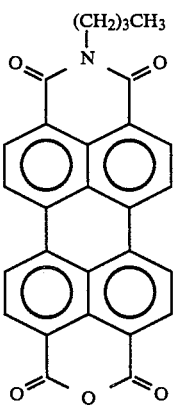

22.4 g of the mono-potassium salt of perylenetetracarboxylic acid monoanhydride are introduced into a solution of 14.6 g of butylamine in 250 ml of water at room temperature, and the mixture is stirred at 20°-25° C. for 5 hours and at 90° C. for 1 hour. The reaction product is then precipitated under acid conditions and isolated. In order to separate off small amounts of diimide and perylenetetracarboxylic acid, the substance is dissolved in 350 ml of 5% strength potassium hydroxide solution at 90°-95° C. and the di-potassium salt is precipitated by adding 30 g of potassium chloride. The salt is filtered off at room temperature and washed with an aqueous solution of 14% of potassium chloride and 1% of potassium hydroxide. The residue is dissolved in water at the boiling point and the solution is clarified from traces of diimide. 19.4 g (86.8%) of perylenetetracarboxylic acid monoanhydride monobutylimide are obtained by acidification of the filtrate and customary isolation.

Analysis: calculated: N 3.1% found: N 3.1%

EXAMPLE 17

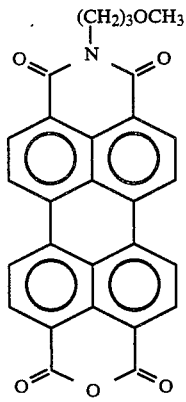

22.4 g of the mono-potassium salt of perylenetetracarboxylic acid monoanhydride are reacted with 19.6 g of 3-methoxypropylamine as described in Example 16. Before the acid precipitation, the mixture is clarified, after dilution with 500 ml of water, from a small amount of diimide. 22.0 g (95.0%) of reaction product are obtained.

Analysis: calculated: N 3.0% found: N 2.7%

EXAMPLE 18

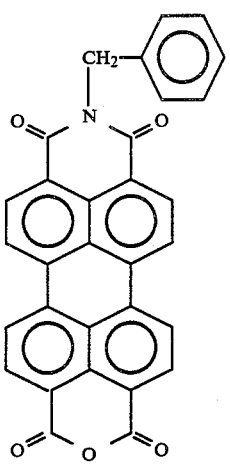

44.8 g of the mono-potassium salt of perylenetetracarboxylic acid monoanhydride are introduced into an ice-cold solution of 47 g of benzylamine in 500 ml of water, the mixture is warmed slowly to 90°–95° C. and, after 2 hours, 60 g of 50% strength potassium hydroxide solution are added and the di-potassium salt is salted out with 25 g of potassium chloride. After working up according to Example 17, perylenetetracarboxylic acid monoanhydride monobenzylimide is obtained in a yield of 44.0 g (91.5%).

Analysis: calculated: N 2.9% found: N 2.6%

EXAMPLE 19

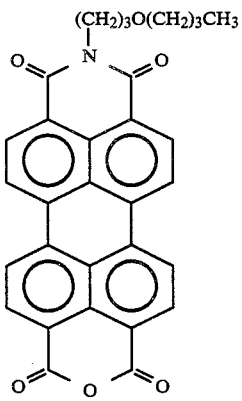

The procedure followed is as according to Example 17, 28.8 g of butoxypropylamine being employed instead of 3-methoxypropylamine. The reaction product is obtained in a yield of 22.6 g (89.5%).

| Analysis: | | | | |
|---|---|---|---|---|
| calculated: | C 73.7% | found: | C 73.3% |
| | H 4.5% | | H 4.5% |
| | N 2.8% | | N 2.7% |

EXAMPLE 20

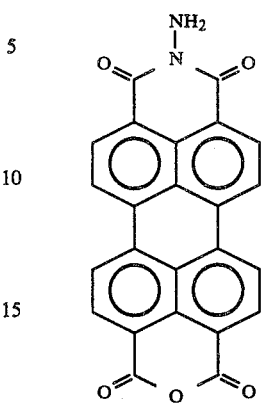

A mixture of 300 ml of water, 13.8 g of hydrazine hydrate (80% strength) and 22.4 g of the mono-potassium salt of perylenetetracarboxylic acid monoanhydride is warmed to 90° C. and is kept at this temperature for 3 hours. It is then diluted with 500 ml of water and clarified hot. The reaction product, which has been precipitated from the filtrate with acid and isolated in the customary manner, is converted into the di-potassium salt by treatment with 400 ml of hot 5% strength potassium hydroxide solution. After customary working up, 18.2 g (89.7%) of perylenetetracrboxylic acid monoanhydride mono-N-aminoimide are obtained.

| Analysis: | | | | |
|---|---|---|---|---|
| calculated: | C 70.9% | found: | C 70.4% |
| | H 2.5% | | H 2.4% |
| | N 6.9% | | N 6.9% |

EXAMPLE 21

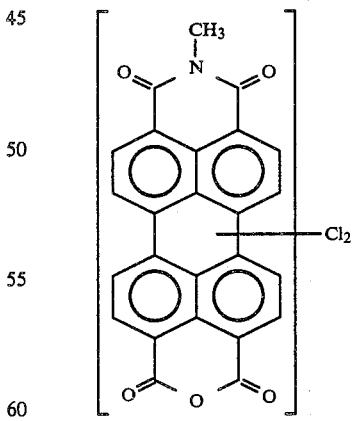

Following the procedure of Example 16, 20.7 g of the mono-potassium salt of dichloroperylenetetracarboxylic acid monoanhydride, prepared from dichloroperylenetetracarboxylic acid dianhydride according to Example 10, in 250 ml of water are reacted with 10.8 g of 45.4% strength methylamine solution to give the corresponding monoanhydride monomethylimide.

Yield: 10.4 g (54.8%)
Analysis: calculated: N 3.0% found: N 3.1%

EXAMPLE 22

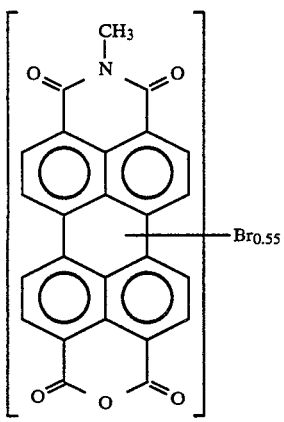

21.1 g of the mono-potassium salt of bromoperylenetetracarboxylic acid monoanhydride, prepared according to Example 9, are suspended in 250 ml of water, and 9.8 g of methylamine solution (45.4% strength) are added. The mixture is subsequently stirred at 20°–25° C. for 2 hours, and 28 g of 50% strength potassium hydroxide solution are then allowed to run in. The mixture is kept at 90° C. for 1 hour and then cooled to 20° C. and filtered. The reaction product is isolated in a yield of 16.5 g (92%) according to Example 16, from the di-potassium salt thus obtained.

| Analysis: | | | |
|---|---|---|---|
| calculated: | Br 9.8% | found: | Br 10.3% |
| | N 3.1% | | N 3.3% |

The table which follows contains further perylene-3,4,9,10-tetracarboxylic acid monoanhydride monoimides, which are obtained by procedures corresponding to those described in the above examples:

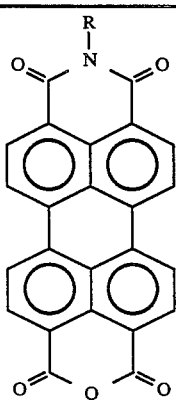

| | | Analysis | |
|---|---|---|---|
| Example | R | calculated | found |
| 23 | —(CH$_2$)$_7$CH$_3$ | 2.8% N | 2.9% N |
| 24 | —(CH$_2$)$_3$OCH$_2$CH(C$_2$H$_5$)(CH$_2$)$_3$CH$_3$ | 2.5% N | 2.7% N |
| 25 | —CH$_2$CH(OH)CH$_3$ | 3.1% N | 3.0% N |
| 26 | —(CH$_2$)$_2$N(C$_2$H$_5$)$_2$ | 5.7% N | 5.5% N |
| 27 | —(CH$_2$)$_3$—N(morpholine) | 5.4% N | 5.1% N |
| 28 | —OH | 3.4% N | 3.5% N |
| 29 | —CH$_2$—C$_6$H$_4$—CH$_3$ | 2.8% N | |
| 30 | —CH$_2$—C$_6$H$_4$—Cl | 6.9% Cl | |

We claim:
1. A compound of the formula

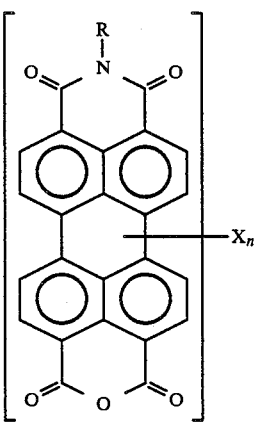

in which R is hydrogen, amino, cycloalkyl of 4 to 8 carbon atoms, or alkyl of 1 to 8 carbon atoms which is unsubstituted or substituted by cycloalkyl of 4 to 8 carbon atoms, cyano, hydroxy, carbamoyl, lower dialkylamino, morpholyl, phenyl which is unsubstituted or substituted by halogen or lower alkyl, or alkoxy of 1 to 8 carbon atoms which is unsubstituted or substituted by lower alkoxy;

X is chlorine or bromine;

n is a number from 0 to 2; and

R is not hydrogen or unsubstituted alkyl when n is the number 0.

2. The compound, as claimed in claim 1, in which R is hydrogen, amino or alkyl of 1 to 8 carbon atoms which is substituted by by hydroxy, lower dialkylamino, morpholyl, alkoxy of 1 to 8 carbon atoms or phenyl which is unsubstituted or substituted by halogen or lower alkyl; X is chlorine or bromine; n is a number from 0 to 2.

3. The compound as claimed in claim 1 in which R is amino, cycloalkyl of 4 to 8 carbon atoms or alkyl of 1 to 8 carbon atoms which is substituted by cycloalkyl of 4 to 8 carbon atoms, cyano, hydroxy, carbomoyl, lower dialkylamino, morpholyl, phenyl which is unsubstituted or substituted by halogen or lower alkyl, or alkoxy of 1 to 8 carbon atoms which is unsubstituted or substituted by lower alkoxy.

4. The compound as claimed in claim 1 in which n is 1 or 2.

* * * * *